United States Statutory Invention Registration [19]

[11] Reg. Number: H623

Miyazako [43] Published: Apr. 4, 1989

[54] INTEGRAL MULTILAYER ANALYSIS ELEMENT

[75] Inventor: Takushi Miyazako, Saitama, Japan

[73] Assignee: Fuji Photo Film Co., Ltd., Minami-ashigara, Japan

[21] Appl. No.: 155,421

[22] Filed: Feb. 12, 1988

[30] Foreign Application Priority Data

Feb. 12, 1987 [JP] Japan ..... 62-30211

[51] Int. Cl.[4] ..... G01N 31/22

[52] U.S. Cl. ..... 456/170; 422/56; 422/57; 422/58

*Primary Examiner*—John F. Terapane
*Assistant Examiner*—Susan Wolffe
*Attorney, Agent, or Firm*—Sughrue, Mion, Zinn, Macpeak & Seas

[57] ABSTRACT

Disclosed in an integral multilayer analysis element comprising in order, first at least one reagent layer and second a porous spreading layer laminated on a light-transmissive water-impermeable support, wherein a fluorine-containing surfactant is incorporated at least in said spreading layer. The element is especially suitable for clinical examination of an aqueous liquid sample of a human humor such as blood, lymphatic liquid, saliva, urine, etc. By the incorporation of the F-containing surfactant, the spreadable area can be controlled over a broad range of the spotting amount of a sample liquid without interfering with the metering function of the spreading layer.

10 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

INTEGRAL MULTILAYER ANALYSIS ELEMENT

FIELD OF THE INVENTION

The present invention relates to an improved dry-type, integral multilayer analysis element for analyzing predetermined component(s) in an aqueous liquid sample, and more precisely, to a integral multilayer analysis element useful for clinical examination of an aqueous liquid sample, especially a biotic humor such as blood, lymphatic fluid, saliva, urine, etc.

BACKGROUND OF THE INVENTION

As one form of a dry analysis element, numerous kinds of integral multilayer analysis elements (hereinafter often referred to as a "multilayer analysis element") have been proposed which are formed by laminating a water-absorbing coloring reagent layer comprising a coloring reagent dispersed in a hydrophilic polymer binder, on a transparent light-transmissive water-impermeable support, and laminating a porous spreading layer (hereinafter often referred to as a "spreading layer") adhered thereover as an outermost layer. The spreading layer of the multilayer analysis element is a layer having the function of spreading an aqueous liquid sample (for example, blood such as whole blood, plasma, and serum, lymphatic fluid, saliva, spinal fluid, vaginal fluid, urine, drinking water, alcoholic drinks, river water, various drainages, etc). The aqueous liquid sample spotted on the upper surface of the element (which is in the side remote from the transparent support) is spreaded to the surface direction without substantially localizing the components contained in the liquid sample so that the thus spreaded liquid sample may be transferred into the water-absorbing hydrophilic polymer binder and layer, which is typically a water-absorbing coloring reagent layer, almost at a constant ratio per unit surface area. This function of the spreading layer is referred to as a metering function.

Japanese Patent Application (OPI) No. 6167/87 (the term "OPI" as used herein means a "published unexamined Japanese patent application") describes a integral multilayer analysis element for determination of total lactic dehydrogenase, which contains a fluorinated surfactant. In the multilayer analysis element, a fluorinated surfactant is incorporated into one or more layers of the spreading layer, subbing layer, reagent layer and registration layer, whereby an improvement in accuracy (that is, a decrease of the deviation coefficient value caused by contingent error) could be attained. However, the porous spreading layer in the multilayer analysis element is limited only to a non-fibrous isotropic porous spreading layer, such as a fine continuous pore-containing non-fibrous isotropic porous spreading layer formed by polymer microbeads, glass microbeads or diatomaceous earth supported by a hydrophilic polymer binder (as described in Japanese Patent Publication No. 21677/78, U.S. Pat. No. 3,992,158, etc.) or a fine continuous pore-containing porous layer formed by adhering polymer microbeads in a spot-like manner with a polymer adhesive which does not swell with water (that is, a three-dimensional lattice-like granule-structural layer, as described in Japanese Patent Application (OPI) No. 90859/80).

It is known that the addition of a surfactant, preferably a nonionic surfactant such as p-nonyl phenoxy polyethoxy ethanol, etc., to the spreading layer is effective for improving the metering function of the layer with respect to the aqueous liquid sample to be tested. However, it is also known that the range of the metering function which can be improved by the addition of the nonionic surfactant is narrow.

On the other hand, the improvement of accuracy (that is, a decrease of the deviation coefficient value caused by contingent error) in the integral multilayer analysis element for determination of total lactic dehydrogenase (LDH) described in Japanese Patent Application (OPI) No. 6167/87, which contains fluorinated surfactant is caused by the association of the fluorinated surfactant with the reaction between the LDH, which is an analyte (that is, a component to be analyzed), and a substrate for LDH, in the system comprising the combination of the non-fibrous isotropic porous spreading layer and the fluorinated surfactant, whereby the analysis accuracy is improved within the range of a low LDH level.

SUMMARY OF THE INVENTION

One object of the present invention is to provide a integral multilayer analysis element having a porous spreading layer which can control the spreading area over a broad range of the spotting amount of a liquid sample without interfering with the spreading (metering) function of the layer.

Another object of the present invention is to provide a multilayer analysis element with an increased quantitative analysis accuracy, which has a porous spreading layer capable of controlling the spreadable area over a broad range of the spotting amount of a liquid sample without interfering with the spreading (metering) function of the layer, irrespective of the kind of materials used to construct the spreading layer.

Still another object of the present invention is to provide a multilayer analysis element with an increased quantitative analysis accuracy, having a porous spreading layer which is made of a fibrous cloth (woven or knitted fabric) and which can control the spreadable area over a broad range of the spotting amount of a sample liquid without interfering with the metering function of the layer.

A further object of the present invention is to provide a multilayer analysis element, which has a spreading layer capable of controlling the spreadable area over a broad range of the spotting amount of a sample liquid without interfering with the metering function of the layer and which can be used for practical quantitative analysis of trace components in a biotic humor with high accuracy.

In order to attain these and other objects, the present invention provides a integral multilayer analysis element comprising, in order, first at least one reagent layer and second a porous spreading layer laminated on a light-transmissive water-impermeable support, wherein a fluorine-containing surfactant is incorporated at least in the spreading layer.

DETAILED DESCRIPTION OF THE INVENTION

As the light-transmissive water impermeable support for the integral multilayer analysis element of the present invention there can be used any light-transmissive (or transparent) and water-impermeable support used for conventional known multilayer analysis elements. Examples of the support include a film-like (or sheet-like) or plate support made of a polymer such as polyethylene terephthalate, polycarbonate of bisphenol A, polystyrene, cellulose esters (e.g., cellulose diacetate, cellulose triacetate, cellulose acetate propionate, etc.), etc., The support has a thickness preferably of from about 50 μm to about 1 mm, more preferably from about 80 μm to about 300 μm, and has a transparent and smooth surface such that this may transmit at least electromagnetic radiation having a wavelength falling within a part of the range of from about 200 nm to about 900 nm. If desired, any known subbing layer or adhesive layer can be provided on the surface of the support so as to strengthen the adhesion between the water-absorbing layer or coloring reagent layer to be provided on the support and the support.

The reagent layer is a substantially non-porous and water-absorbing layer or a fine porous and water-permeable layer containing one reagent or a reagent composition comprising plural reagent components (hereinafter generically referred to as a "reagent composition or reagent"), which can react with the component to be analyzed (analyte) in an aqueous liquid sample to cause a detectable variation, and a hydrophilic polymer binder. A "detectable variation" is generally a variation which can be detected by optical measurement, for example, color variation, coloration fluorescence generation, variation of the absorption wavelength within the ultraviolet range, turbidity generation, etc.

The composition of the reagent in the reagent layer is determined on the basis of the analyte in the aqueous liquid sample to be examined and the method selected for analyzing the analyte e.g., simple chemical reaction, biochemical or chemical reaction partisipated (catalyzed) with an enzyme, etc. When the thus selected chemical reaction is a reaction involving two or more reagent components or enzymes, the plural reagent components or enzymes can be incorporated into one reagent layer in mixture or, alternatively, the plural reagent components or enzymes can be incorporated individually into two or more layers. Examples for the reagent composition to be incorporated into the reagent layer include the enzyme-containing reagent compositions described in the aforesaid patent publications as well as other known reagent compositions for analysis and reagent compositions for clinical diagnosis, etc.

Examples of enzyme-containing reagent compositions include the improved trinder reagent compositions for glucose analysis containing glucose oxidase and peroxidase, which are described in U.S. Pat. No. 3,992,158, Japanese Patent Publication No. 21677/78, Japanese Patent Application (OPI) Nos. 26793/79, 164356/80, 20853/84, 46854/84 and 54962/84, Japanese Patent Publication No. 25840/80, etc.; the reagent compositions for cholesterol analysis containing cholesterol oxidase, peroxidase and optionally cholesterol esterase, which are described in Japanese Patent Publication No. 45599/81, Japanese Patent Application (OPI) No. 193352/84, etc.; the reagent compositions for urea-form nitrogen (BUN) analysis containing urease, which are described in Japanese Patent Application (OPI) Nos. 3488/77, 77661/83 and 70460/81, etc.; the reagent compositions for triglyceride or glycerol analysis containing lipoprotein lipase, glycerol kinase, α-glycerol 3-phosphate oxidase or peroxidase, which are described in Japanese Patent Application (OPI) No. 24893/78, etc.; the reagent compositions for billirubin analysis containing billirubin-specific oxidase and peroxidase, which are described in Japanese Patent Application (OPI) Nos. 151193/79 and 78580/85, etc.; the reagent compositions for uric acid analysis containing uricase and peroxidase, which are described in Japanese Patent Application (OPI) Nos. 26188/78 and 193352/84, etc.; the coloring reagent compositions for hydrogen peroxidase detection containing peroxidase, which are described in Japanese Patent Application OPI Nos. 24499/80 and 86457/83, etc.

The hydrophilic polymer binder to be used in the substantially non-porous and water-absorbing reagent layer (hereinafter often referred to as the "non-porous reagent layer") functions at least as a medium for substantially uniformly dissolving or dispersing the reagent composition and can further function to absorbs the water in the aqueous liquid sample so as to reach the analyte together with the water to the reagent layer. The hydrophilic polymer binder that can be used is the same as the hydrophilic polymer binder that can be used in the water-absorbing layer which will be described hereinafter.

The dry thickness of the non-porous reagent layer is preferably from about 3 μm to about 50 μm, more preferably from about 5 μm to about 40 μm, and the amount of the layer coated is preferably from about 3 $g/m^2$ to about 50 $g/m^2$, more preferably from about 5 $g/m^2$ to about 40 $g/m^2$.

The microporous and water-permeable reagent layer is one containing the reagent composition in a microporous structural layer made of fine solid grains and a hydrophilic polymer binder or in fibrous or non-fibrous microporous structural layer the same as that used for the porous spreading layer which will be described hereinafter. The microporous structural layer made of fine solid grains and a hydrophilic polymer binder, as herein referred to, means a structural layer made by combining microporous fine grains or non-porous fine grains with a hydrophilic polymer binder to give a microporous and continuous fine pore-containing structure, which is the reagent layer described in Japanese Patent Application (OPI) Nos. 120957/84, 145965/84 and 222770/85, etc. The dry thickness of the microporous reagent layer is, when the layer is composed of solid fine grains and a hydrophilic polymer binder, preferably from about 7 μm to about 50 μm, more preferably from about 10 μm to about 40 μm; or when the layer is microporous structural comprising fibrous or non-fibrous the same layer as that to be used as the porous spreading layer is described hereinafter, the thickness thereof is preferably from about 50 m to about 300 μm, more preferably from about 80 μm to about 250 μm.

To the reagent layer of any type can be added known pH buffers, organic carboxylic acids, acid polymers, basic polymers, etc. so as to adjust the pH value of the element during the analysis operation. In addition, the reagent layers can further contain known mordant agents, polymer mordant agents, etc.

The non-porous reagent layer can be provided on the light-transmissive and water-impermeable support by any known coating method, for example, as described in the aforesaid patent publications. The microporous reagent layer can be provided on the support by the method described in Japanese Patent Application (OPI) Nos. 120957/84 and 145965/84, etc. If desired, the surface of the support can be processed by known physicochemical activation treatments or chemical activation treatments or a transparent subbing layer (such as a gelatin subbing layer) can be provided on the support, so that the adhesive force between the support and the reagent layer can be strengthened.

In the multilayer analysis element of the present invention, a water-absorbing layer can be provided between the support and the reagent layer. The water-absorbing layer is a layer consisting mainly of a hydrophilic polymer, which can absorb water to be swelled, and specifically, this is a layer capable of absorbing the water in the aqueous liquid sample which has reached or penetrated to the interface of the water-absorbing layer (i.e., the upper side of the water-absorbing layer). When a complete blood sample is to be examined, the water-absorbing layer acts to accelerate the permeation of the aqueous liquid component plasma into the lower non-fibrous porous sheet (porous reagent layer). The hydrophilic polymer to be used in the water-absorbing layer is a polymer which has, after absorbing water, a swelling ratio preferably of from about 150 % to about 2000 %, more preferably from about 250 % to about 1500 %, at 30° C. Examples of the hydrophilic polymer include the gelatins, such as acid-processed gelatin, deionized gelatin, etc., and the gelatin derivatives, such as phthalated gelatin, hydroxyacrylate-grafted gelatin, etc., described in Japanese Patent Application (OPI) Nos. 171864/84 and 115859/85, etc.; and the agarose, pullulane, pullulane derivatives, a polyacrylamide, a polyvinyl alcohol, a polyvinyl pyrrolidone, etc. described in Japanese Patent Application (OPI) Nos. 171864/84, 115859/85, etc. These hydrophilic polymers can be used singly or in a combination of two or more. Although gelatins or gelatin derivatives are generally preferred for the water-absorbing layer, hydrophilic polymers of protein derivatives except gelatins and polyacrylamide, polyvinyl alcohol, etc. are preferably used when the analyte is albumin, total protein, etc.

The dry thickness of the water-absorbing layer is preferably from about 1 μm to about 100 μm, more preferably from about 3 μm to about 30 μm; and the coated amount thereof is preferably from about 1 g/m$^2$ to about 100 g/m$^2$, more preferably from about 3 g/m$^2$ to about 30 g/m$^2$. To the water-absorbing layer can be added known pH buffers, organic carboxylic acids, acid polymers, basic polymers, etc. so as to adjust the pH value of the element during the actual use thereof (or during the analysis operation therewith). In addition, the water-absorbing layer can further contain known mordant agent, polymer mordant agents, etc.

Although the reagent layer and the water-absorbing layer are preferred to be substantially transparent, titanium dioxide grains, barium sulfate grains, carbon black, etc. can be added to the reagent layer or the water-absorbing layer each in a small amount, if desired, so as to adjust the optical characteristics of the element.

As the porous spreading layer these can be used the woven fabric spreading layer (for example, plain weave fabric such as broad cloth, poplin, etc.) described in Japanese Patent Application (OPI) Nos. 164356/80 and 66359/82, etc. the knitted fabric spreading layer (for example, tricot fabric, double tricot fabric, milanese fabric, etc.) described in Japanese Patent Application (OPI) No. 222769/85, etc.; the spreading layer made of an organic polymer fiber pulp-containing paper, which is described in Japanese Patent Application (OPI) No. 148250/82, etc.; the non-fibrous isotropic porous spreading layer, for example a membrane filter (brushed polymer layer), a continuous micro pore-containing porous layer, where polymer micro-beads, glass micro-beads or diatomaceous earth is(are) supported by a hydrophilic polymer binder, which is described in Japanese Patent Publication No. 21677/78, U.S. Pat. No. 3,992,158, etc.; the non-fibrous isotropic porous spreading layer comprising a continuous micro pore-containing porous layer (three-dimensional lattice-like granule-structural layer) formed by bonding polymer micro beads in point-to-point contact with a polymer adhesive unswellable with water, which is described in Japanese Patent Application (OPI) No. 90859/80, etc.

Among these porous spreading layers, the fibrous spreading layers such as woven fabric spreading layer and knitted fabric spreading layer are preferred for the embodiment wherein the reagent composition is present in the spreading layer (that is, one kind of microporous reagent layer-containing embodiments), because of the easiness of the incorporation of the reagent composition into the spreading layer. In this embodiment, it is preferred to provide the spreading layer on a water-absorbing layer either directly or via a light shielding layer or an adhesive layer.

The woven fabric or knitted fabric to be used for the porous spreading layer can be treated by physical activation such as glow discharge treatment or corona discharge treatment, as described in Japanese Patent Application (OPI) No. 66359/82, at least on one surface of the fabric, or can also be treated by hydrophilicity-imparting treatments such as water-washing and degreasing treatments, impregnation in a hydrophilic polymer or a combination thereof in an appropriate order, as described in Japanese Patent Application (OPI) Nos. 164356/80 and 66359/82, etc., so as to make the fabric hydrophilic, whereby the adhesion force between the fabric layer and the lower layer (which is nearer to the support) can be strengthened.

A color-shielding layer or a light-reflecting layer can be provided between the reagent layer or water-absorbing layer and the spreading layer. The color-shielding layer or the light-reflecting layer is a layer containing white fine grains such as titanium dioxide fine grains, barium sulfate fine grains, etc., which have a light-shieldability or both a light-shieldability and light-reflectability, as dispersed in a hydrophilic polymer binder such as gelatin, etc., and the layer preferably has a dry thickness of from about 2 μm to about 20 μm.

In addition, a known adhesive layer comprising a hydrophilic polymer such as gelatin can further be provided on the reagent layer, water absorbing layer, color-shielding layer or light-reflecting layer, for the purpose of firmly adhering and integrating the spreading layer. The dry thickness of the adhesive layer is preferably from about 0.5 μm to about 5 μm.

In the integral multilayer analysis element of the present invention, an adequately selected known buffer, which can buffer the pH value of the element to a desired value within the range of from 2.0 to 10.0, during the actual analysis operation by application of a liquid sample to the element, can be incorporated into one or more layers of the porous spreading layer, reagent layer, water-absorbing layer, adhesive layer, light-shielding layer, etc.

The buffers to be used for this purpose can be selected from the pH buffer system described in *Handbook for Chemistry, Fundamental Course* (by Japan Chemical Association, published by Maruzen Publishing Co., Japan, 1966), pages 1312–1320; R. M. C. Dawson et al, *Data for Biochemical Research,* 2nd Ed. (Oxford at the Clarendon Press, 1969), pages 476–508; *Biochemistry,* 5, pages 467–477 (1966); *Analytical Biochemistry,* 104, page 300–310 (1980), etc.

Examples of the pH buffers capable of adjusting the pH value to the range of from 2.0 to 10.0 include buffers containing tris(hydroxymethyl)aminomethane (Tris); buffers containing phosphates; buffers containing borates; buffers containing citric acid or citric acid salts; buffers containing glycine; N,N-bis(2-hydroxyethyl)glycine (Bicine); sodium salt or potassium salt of N-2-hydroxyethylpiperazine-N'-2-hydroxypropane-3-sulfonic acid (HEPPS); sodium salt or potassium salt of N-2-hydroxyethyl-piperazine-N'-3-sulfonic acid (EPPS), sodium salt or potassium salt of N-[tris(hydroxymethyl)methyl]-3-aminopropane-sulfonic acid (TAPS), sodium salts or potassium salt of N-2-hydroxyethylpiperazine-N'-2-ethanesulfonic acid (HEPES); and mixtures of anyone of the buffers and necessary acids, alkalis or salts. Preferred examples of the buffers are potassium dihydrogen phosphate-disodium hydrogen phosphate; Tris-sodium borate; Tris-sodium borate-EDTA disodium salt; Tris-citric acid; acetic acid-sodium acetate; citric acid-sodium dihydrogen phosphate; Bicine; HEPPS; HEPPS sodium salt; EPPS; EPPS sodium salt; TAPS; TAPS sodium salt, etc.

The fluorine-containing surfactant to be incorporated into the porous spreading layer or the reagent composition-containing porous spreading layer in the integral multilayer analysis element of the present invention is a fluoroalkyl group-containing organic compound having a surface tension preferably of about 45 dyne/cm or less, more preferably about 30 dyne/cm or less, in the form of a 0.1 w/w % aqueous solution at 25° C. As the examples of the fluorine-containing surfactants, there may be mentioned the known fluoroalkyl group-containing organic compounds described in Takahashi, Namba, Koike and Kobayashi, *Handbook of Surfactants* (published by Kogaku Tosho, Tokyo, Japan), 8th Ed. pages 30–34, etc. Among fluorolkyl groups, the preferred one is a perfluoroalkyl group having 3 or more carbon atoms. Examples of the fluorine-containing surfactants include sulfonic acids or their salts, carboxylic acids or their salts, (e.g., salts of an alkali metal such as Li, Na and K), sulfonamides, alkylpolyethoxy ethanols, betaine compounds, quaternary ammonium salts and dibasic carboxylic acid monoesters, which contain at least one perfluoroalkyl group having 3 or more carbon atoms. Specific examples of the fluorine-containing surfactants are mentioned below. In the following chemical formulae, Me represents methyl group, Et represents an ethyl group, Pr represents a propyl group and —Phn— means phenylene group.

(1) Carboxylic acids and their salts, containing at least one perfluoroalkyl group having 3 or more carbon atoms:

$C_6F_{13}COOH$ $C_7F_{15}COOH$ $C_8F_{17}COOH$ $C_{10}F_{21}COOH$ $(CF_3)CF(CF_2)_4COOH$ $C_{11}F_{23}COOH$ $(CF_3)_2(CF_2)CH{=}CHCH_2COOH$ $C_7F_{15}$—Phn—COOH

Sodium, potassium and lithium salts of the above-mentioned compounds.

(2) Sulfonic acids and their salts, containing at least one perfluoroalkyl group having 3 or more carbon atoms:

$C_8F_{17}SO_3H$ $C_9F_{19}SO_3H$ $C_{11}F_{23}SO_3H$ $C_8F_{17}$—Phn—$SO_3H$ $C_9F_{19}$ —Phn—$SO_3H$

Sodium, potassium and lithium salts of the above-mentioned compounds.

(3) Sulfonamide compounds containing at least one perfluoroalkyl group having 3 or more carbon atoms:

$$C_9H_{19}-SO_2-\underset{\underset{Pr}{|}}{N}-CH_2COOK$$

$$C_8F_{17}-SO_2-\underset{\underset{Et}{|}}{N}-(CH_2CH_2O)_nH \qquad \text{(n: average 14)}$$

$$C_{11}F_{23}-SO_2-\underset{\underset{Me}{|}}{N}-(CH_2CH_2O)_nH \qquad \text{(n: average 15)}$$

(4) Alkylpolyethoxy ethanol compounds containing at least one perfluoroalkyl group having 3 or more carbon atoms:

| | |
|---|---|
| $C_7F_{15}CH_2O-(CH_2CH_2O)_nH$ | (n: average 15) |
| $C_{11}F_{23}CH_2O-(CH_2CH_2O)_nH$ | (n: average 30) |
| $C_3F_7CH_2O-(CH_2CH_2O)_nH$ | (n: average 5) |
| $C_9F_{19}COOCH_2CH_2O-(CH_2CH_2O)_nH$ | (n: average 15) |

(5) Betaine type compounds containing at least one perfluoroalkyl group having 3 or more carbon atoms:

$$C_8F_{17}-SO_2NH-(CH_2)_3-\underset{\underset{CH_2CH_2COO^-}{|}}{N^+}Me_2$$

$$C_9F_{19}-CONH-(CH_2)_3-\underset{\underset{CH_2COO^-}{|}}{N^+}Me_2$$

(6) Quaternary ammonium salt compounds containing at least one perfluoroalkyl group having 3 or more carbon atoms:

$C_7F_{15}-CONH-(CH_2)_3-N^+Me_3.I^-$ $C_8F_{17}-SO_2NH-(CH_2)_3-N^+Me_3.CI^-$ (7) Dibasic carboxylic acid monoester compounds containing at least one perfluoroalkyl group having 3 or more carbon atoms:

$$C_6F_{13}-CH_2OCOCH\underset{\underset{HCCOOH}{\|}}{}$$

Sodium, potassium and lithium salts of the compound.

The fluorine-containing compounds having at least one perfluoroalkyl group, which can be used as the fluorine-containing surfactant in the multilayer analysis element of the present invention, are not limited only to the above-mentioned compounds but any other fluorine-containing compounds having the surface tension of the solution which falls within the above-mentioned range can be used in the present invention. Two or more of the fluorine-containing compounds can be blended, or two or more of the mixtures can be used. The content of the fluorine-containing surfactant in the porous spreading layer or the reagent composition-containing porous spreading layer is preferably from about 1 mg/m$^2$ to about 10.0 g/m$^2$, more preferably from about 10 mg/m$^2$ to about 5.0 g/m$^2$.

For the means of incorporating the fluorine-containing surfactant into the porous spreading layer, there may be mentioned a method in which a porous structural sheet material (such as woven fabric, knitted fabric, membrane filter, etc.) for the spreading layer is dipped in a solution containing the fluorine-containing surfactant and then dried so as to introduce the fluorine-containing surfactant into the said porous structural sheet material, and thereafter the sheet material is stuck to and integral with the reagent layer, adhesive layer or light-shielding layer; a method in which a solution of the fluorine-containing surfactant is sprayed (overcoated) over the porous spreading layer of a finished multilayer analysis element and then the solvent is dried and removed so as to keep the fluorine-containing surfactant in the spreading layer, etc. In any method, water, an organic solvent (such as methanol, ethanol, acetone, etc.) or a mixed solvent comprising water and the organic solvent can be used as a solvent for dissolving the fluorine-containing surfactant.

The fluorine-containing surfactant can be used together with any other surfactant(s). As an example of the surfactants which can be used together with the fluorine-containing surfactant, a nonionic surfactant can be mentioned.

A surfactant can be incorporated into the reagent layer, water-absorbing layer, color-shielding or light-reflective layer, adhesive layer, spreading layer, reagent composition-containing spreading layer, etc. As an example of the surfactants, a nonionic surfactant can be mentioned. Specific examples of the nonionic surfactants include p-octyl phenoxy polyethoxy ethanol, p-nonyl phenoxy polyethoxy ethanol, polyoxyethylene oleylether, polyoxyethylene sorbitanmonolaurate, p-nonyl phenoxy polyglycidol, ocytl glucoside, etc. By the incorporation of the nonionic surfactant into the spreading layer together with the fluorine-containing surfactant, the spreading (metering) function of the aqueous liquid sample for examination can be improved. In addition, by the incorporation of the nonionic surfactant into the reagent layer or water-absorbing layer, the water in the aqueous liquid sample can be absorbed substantially uniformly with ease into the reagent layer or the water-absorbing layer during the actual analysis operation, whereby contact of the liquid with the spreading layer can be promoted rapidly and substantially uniformly.

The multilayer analysis element of the present invention can be prepared by known methods described in the above-mentioned patent publications.

It is preferred that the multilayer analysis element of the present invention be cut into a small piece of a cubic form having an edge length of from about 15 mm to about 30 mm or a circle having the same size and is cased in a slide frame, as described in Japanese Patent Publication No. 28331/82, Japanese Utility Model Application (OPI) No. 142454/81, Japanese Patent Application (OPI) No. 63452/82, Japanese Utility Model Application (OPI) No. 32350/83, Jpanese Patent Application Publication 501144/83, etc., so as to be used in the form of a chemical analysis slide, from the viewpoints of manufacture, package, transportation, storage, measurement operation, etc. If appropriate for the object of the use, the element can also be used in the form of a long tape as cased in a cassette or magazine, or can further be used in the form of a small piece as stuck to or cased in a card having an opening.

The multilayer analysis element of the present invention can be employed for analysis of the intended components in a liquid sample to be examined, in accordance with the operation means described in the above-mentioned patent publications. Specifically, an aqueous liquid sample, such as complete blood, plasma, serum, etc. is spotted on the spreading layer in an amount of from about 5 μl to about 30 μl, preferably from about 8 μl to about 15 μl, and incubated thereon for a period of time of from 1 minute to 10 minutes at a substantially constant temperature of from about 20° C. to about 40° C., preferably at a substantially constant temperature of about 37° C. or so, and the optical density of the reagent spreading layer is measured by reflection from the side of the light-transmissive support by the use of light having a maxiumn absorption wavelength or that approximate to the wavelength of the color, fluorescence, turbidity or ultraviolet ray in the inside of the element, and thus the content of the component to be measured in the liquid sample can be obtained by the use of a previously prepared calibration curve on the basis of the principle of colorimetrical analysis. If the amount of the aqueous liquid sample to be spotted and the time and the temperature for the incubation are made constant, quantitative analysis of the component in the sample can be carried out with high accuracy. The measurement operation can be carried out extremely easily and highly accurately by the use of the chemical analysis apparatus described in Japanese Patent Application (OPI) Nos. 77746/81, 21566/83 and 161867/83, etc.

The following examples are intended to illustrate the present invention but not to limit it in any way.

EXAMPLE 1 and COMPARATIVE EXAMPLE 1

A pH buffe-containing water absorbing layer was provided on a colorless transparent polyethylene terephthalate (PET) film (support) having a thickness of 180 μm, by coating an aqueous solution containing the following components on the support and then drying the same.

pH buffer-containing water-absorbing layer composition:

Malic Acid: 3.0 g/m$^2$

The pH value was adjusted to 3.0 with NaOH.

N-vinylpyrrolidone acrylamide-methacryl alcohol (48/48/4 wt.%)

ternary copolymer (hydrophilic binder) 30 g/m$^2$

Next, the pH buffer-containing water-absorbing layer was uniformly wetted with water, and a woven broad cloth made of 100S(yarn count)-corresponding PET spun yarns and having a thickness of 150 μm was stuck thereto and dried to form a porous spreading layer.

A methanol solution containing the indicator and the surfactant(s) which are shown in Table 1 below, was coated over the spreading layer so that the indicator and the surfactant(s) were introduced into the spreading layer. Thus, two kinds of integral multilayer analysis elements (Al and Cl) for quantitative albumin determination were prepared. The element Al is the element of the present invention and the element Cl is a comparative element.

TABLE 1

| Components | Amount Coated Element Al | Amount Coated Element Cl |
|---|---|---|
| Bromocresol Green | 0.6 g/m$^2$ | 0.6 g/m$^2$ |
| $C_7F_{15}CH_2O—(CH_2CH_2O)_n—H$ (n: average 10) | 0.4 g/m$^2$ | — |
| Oleyl Alcohol Polyethylene-oxide Adduct (oxyethylene unit: average 20) | 5.0 g/m$^2$ | 5.0 g/m$^2$ |

A physiological salt solution containing human serum albumin (HSA) in an amount of 1.5%, 3.2%, 4.5% or 6.4% was prepared as an aqueous liquid sample to be examined, and 10 μl of each sample was spotted on the spreading layer of each of the elements Al and Cl and incubated at 37° C. for 6 minutes. After the incubation, the color optical density of the element was measured by reflective measurement from the side of the PET support with a visible ray having a central wavelength of 640 nm, whereupon the area of the aqueous liquid sample as spreaded was measured from the side of the spreading layer. The results obtained are shown in Table 2 below.

TABLE 2

| HSA Concentration (%) | 1.5 | 3.2 | 4.5 | 6.4 |
|---|---|---|---|---|
| Element Al | | | | |
| Area Spreaded (mm$^2$) | 78.5 | 78.9 | 79.8 | 77.6 |
| Color Optical Density | 0.798 | 0.927 | 1.109 | 1.249 |
| Element Cl | | | | |
| Area Spreaded (mm$^2$) | 113 | 115 | 113 | 113 |
| Color Optical Density | 0.786 | 0.907 | 0.961 | 1.017 |

The data of Table 2 demonstrate that the area of the aqueous liquid sample as spreaded in the integral multilayer analysis element for quantitative albumin determination of the present invention, which contained the fluorine-containing surfactant, was smaller than that in the comparative element (prior art), which did not contain the fluorine-containing surfactant, by about 30%, and the color optical density value of the former was larger than that of the latter. As a result, the slope of the calibration curve of the former was larger than the latter by about 90% in average, and therefore the measurement accuracy of the former was improved to be superior to the latter.

EXAMPLE 2 and COMPARATIVE EXAMPLE 2

A biuret reagent layer was provided on a colorless transparent PET film having a thickness of 180 μm, by coating an aqueous solution comprising the following components on the support and then drying the same.

| | |
|---|---|
| LiOH | 9.6 g/m$^2$ |
| $CuSO_4$ | 8.0 g/m$^2$ |
| Disodium Tartarate | 2.9 g/m$^2$ |

-continued

| | |
|---|---|
| Tartaric Acid | 4.5 g/m$^2$ |
| Acrylamide-N—vinylpyrrolidone (50/50 wt. %) Binary Copolymer (hydrophilic binder) | 30 g/m$^2$ |

Next, in the same manner as in Example 1, a woven broad cloth made of 100S-corresponding PET spun yarns and having a thickness of 150 μm was stuck to the reagent layer and dried to form a porous spreading layer on the layer.

A methanol solution containing the surfactant(s) shown in Table 3 below was coated over the spreading layer and dried so that the surfactant(s) was(were) introduced into the spreading layer in an amount shown in Table 3. Thus, two kinds of integral multilayer analysis elements (A2 and C2) for total protein quantitative determination were prepared. The element A2 is the element of the present invention and the element C2 is a comparative element.

TABLE 3

| Components | Amount Coated Element A2 | Amount Coated Element C2 |
|---|---|---|
| $C_7F_{15}COOH$ Perfluorocaprylic Acid | 10 mg/m$^2$ | — |
| Oleyl Alcohol Polyethylene-oxide Adduct (oxyethylene unit: average 20) | 4.5 g/m$^2$ | 4.5 g/m$^2$ |

A physiological salt solution containing bovine serum albumin (BSA) in an amount of 3.1%, 4.2%, 5.5%, 6.6% or 8.7% and a BSA-free physiological salt solution were prepared as an aqueous liquid sample to be examined, and 10 μl of each sample was spotted on the spreading layer of each of the elements A2 and C2 and incubated for 6 minutes at 37° C. After the incubation, the color optical density of the element was measured by reflective measurement from the side of the PET support with a visible ray having a central wavelength of 540 nm, whereupon the area of the aqueous liquid sample as spreaded was measured from the side of the spreading layer. The results obtained are shown in Table 4 below.

TABLE 4

| BSA Concentration in Aqueous Liquid Sample | Color Optical Density Element A2 | Color Optical Density Element C2 | Area Spreaded Element A2 | Area Spreaded Element C2 |
|---|---|---|---|---|
| 0 (Physiological salt solution) | 0.685 | 0.676 | 98.1 | 133 |
| 3.1 % | 0.977 | 0.875 | 97.2 | 130 |
| 4.2 % | 1.052 | 0.930 | 97.7 | 129 |
| 5.5 % | 1.140 | 1.002 | 99.0 | 131 |
| 6.6 % | 1.227 | 1.069 | 98.4 | 131 |
| 8.7 % | 1.341 | 1.163 | 98.0 | 129 |

The data of Table 4 demonstrate that the area of the aqueous liquid sample as spreaded in the integral multilayer analysis element for total protein quantitative determination of the present invention, which contained the fluorine-containing surfactant, was smaller than that in the comparative element (prior art), which did not contain the fluorine-containing surfactant, by about 30%, and the color optical density value of the former was larger than that of the latter. As a result, the slope of the calibration curve of the former was larger than the latter by about 35% in average, and therefore the measurement accuracy of the former was improved to be superior to the latter.

EXAMPLE 3 and COMPARATIVE EXAMPLE 3

A water-absorbing layer was provided on a colorless transparent PET film having a thickness of 180 μm, by coating an aqueous solution containing a deionized gelatin (hydrophilic binder) on the support in an amount of 30 g/m$^2$ and then drying the same.

Next, in the same manner as Example 1, a woven broad cloth made of 100S-corresponding PET spun yarns and having a thickness of 150 μm was stuck to the water-absorbing layer and dried to form a porous spreading layer.

A 1/1 (by volume) water/methanol solution containing the surfactant shown in Table 5 below was coated over the spreading layer and dried so that the surfactant was introduced into the spreading layer in an amount shown in Table 5. Thus, two kinds of integral multilayer analysis elements (A3 and C3) for quantitative haemoglobin concentration analysis were prepared. The element A3 is the element of the present invention and the element C3 is a comparative element.

TABLE 5

| Components | Amount Coated | |
|---|---|---|
| | Element A3 | Element A4 |
| The following F-containing surfactant | 100 mg/m$^2$ | — |
| Oleyl Alcohol-Polyethylene-oxide Adduct (oxyethylene unit: average 20) | — | 100 mg/m$^2$ |
| Chemical formula of the F-containing surfactant: $C_8F_{17}Phn\text{-}SO_2\text{—}(CH_2)_3\text{—}N^+Me_3.Cl^-$ | in which-Phn-represents a phenylene group. | |

A control serum containing a human haemoglobin (HHb) in an amount of 5g/dl, 10g/dl, 15g/dl or 20g/dl and an HHb-free physiological salt solution were prepared as an aqueous liquid sample to be examined, and 10 μl of each sample was spotted on the spreading layer of each of the elements A3 and C3. The color optical density of the element was measured by reflective measurement from the side of the PET support with a visible ray having a central wavelength of 500 nm. The results obtained are shown in Table 6 below. In addition, the area of the aqueous liquid sample as spreaded was also measured from the side of the spreading layer. As a result, the area of the aqueous liquid sample as spreaded in the integral multilayer analysis element for quantitative haemoglobin concentration analysis of the present invention, which contained the fluorine-containing surfactant, was smaller than that in the comparative element (prior art), which did not contain the fluorine containing surfactant, by about 30%.

TABLE 6

| HHb Concentration (g/dl) | Reflective color Optical Density (500 nm) | |
|---|---|---|
| | Element A3 | Element C3 |
| 0 (Physiological salt solution) | 0.280 | 0.281 |
| 5 | 0.652 | 0.581 |
| 10 | 0.961 | 0 850 |
| 15 | 1.254 | 1.102 |
| 20 | 1.537 | 1.338 |

The data of Table 6 demonstrate that the color optical density value in the integral multilayer analysis element for quantitative haemoglobin concentration analysis of the present invention, which contained the fluorine-containing surfactant, was larger than that in the comparative element (prior art), which did not contain the fluorine-containing surfactant. As a result, the slope of the calibration curve of the former was larger than the latter by about 20% in average, and therefore the measurement accuracy of the former was improved to be superior to the latter.

References written in English corresponding to Japanese Patent documents cited in the Detailed Description are shown below.

Japanese Patent Application (OPI) 90859/80: U.S. Pat. No. 4,258,001
Japanese Patent Application (OPI) 164356/80: U.S. Pat. No. 4,292,272
Japanese Patent Application (OPI) 222769/85: EP 0 162 302A
Japanese Patent Application (OPI) 90859/80: U.S. Pat. No. 4,258,001
Japanese Patent Application (OPI) 3488/77: US Re 30,267
Japanese Patent Application (OPI) 222770/85: EP 0 162 301A
Japanese Patent Application (OPI) 120957/84: EP 0 114 403B
Japanese Patent Application (OPI) 145965/84: EP 0 115 873A
Japanese Patent Application (OPI) 171864/84: EP 0 119 861A
Japanese Patent Application (OPI) 66359/82: GBP 2 087 074A
Japanese Patent Application (OPI) 77746/81: U.S. Pat. No. 4,488,810
Japanese Utility Model Application (OPI) 142454/81: U.S. Pat. No. 4,387,990
Japanese Patent Application Publicaiton 501144/83: WO 83/00391
Japanese Patent Publication 21677/78: U.S. Pat. No. 3,992,158
Japanese Patent Publication 25840/80: U.S. Pat. No. 3,886,045
Japanese Patent Publication 45599/81: U.S. Pat. No. 3,983,005
Japanese Patent Publication 28331/82: U.S. Pat. No. 4,169,751

While the invention has been described in detail and with reference to specific embodiments thereof, it will be apparent to one skilled in the art that various changes and modifications can be made therein without departing from the spirit and scope thereof.

What is claimed is:

1. A integral multilayer analysis element comprising, in order, first at least one reagent layer and second a porous spreading layer laminated on a light-permeable water-impermeable support, wherein a fluorine-containing surfactant is incorporated at least in said spreading layer.

2. A integral multilayer analysis element as in claim 1, wherein said fluorine-containing surfactant is a compound selected from the group consisting of sulfonic acids or their salts, carboxylic acids or their salts, sulfonamides, alkylpolyethoxy ethanols, betaine compounds, quaternary ammonium salts and dibasic carboxylic acid monoesters, each of which contains at least one perfluoroalkyl group having at least 3 carbon atoms.

3. A integral multilayer analysis element as in claim 1, wherein said spreading layer is a fibrous spreading layer.

4. A integral multilayer analysis element as in claim 3, wherein said fibrous spreading layer is a fibrous spreading layer made of a fiber selected from the group consisting of a woven fabric and knitted fabric.

5. An integral multilayer analysis element as in any one claims 1 to 4, wherein said spreading layer contains a reagent.

6. An integral muiltilayer analysis element as in claim 1, wherein said fluorine-containing surfactant is a fluoroalkyl group-containing organic compound having a surface tension of not more than 45 dyne/cm, in the form of a 0.1 w/w% aqueous solution at 25° C.

7. A method for analyzing an aqueous liquid smaple of a biotic humor comprising:

(1) spotting a sample suspected of containing an analyte on a spreading layer of a integral multi-layer analysis element, (2) incubating the integral multi-layer analysis element for a period sufficient to cause a detectable reaction, and (3) determining the amount of analyte in the sample:

wherein said integral multi-layer analysis element comprises, in order, first at least one reagent layer and second a porous spreading layer laminated on a light-transmissive water-impermeable support, wherein a fluorine-containing surfactant is incorporated at least in said spreading layer.

8. A method as in claim 7, wherein said fluorine-containing surfactant is selected from the group consisting of sulfonic acids or their salts, carboxylic acids or their salts, sulfonamides, alkylpolyethoxy ethanols, betaine compounds, quaternary ammonium salts and dibasic carboxylic acid monoesters, each of which contains at least one perfluoroalkyl group having at least 3 carbon atoms.

9. A method as in claim 7, wherein said spreading layer is a fibrous spreading layer.

10. A method as in claim 9, wherein said fibrous spreading layer is made of a fabric selected from the group consisting of woven fabric or knitted fabric.

* * * * *